United States Patent [19]

Angevine et al.

[11] Patent Number: 5,073,655

[45] Date of Patent: * Dec. 17, 1991

[54] METHOD FOR PREPARING DIARYLALKANES

[75] Inventors: Philip J. Angevine, Woodbury; Ivy D. Johnson, Medford; David O. Marler, Deptford; John P. McWilliams, Woodbury, all of N.J.

[73] Assignee: Mobil Oil Corp., Fairfax, Va.

[*] Notice: The portion of the term of this patent subsequent to Feb. 12, 2008 has been disclaimed.

[21] Appl. No.: 559,242

[22] Filed: Jul. 27, 1990

Related U.S. Application Data

[63] Continuation-in-part of Ser. No. 254,524, Oct. 6, 1988, Pat. No. 4,954,325, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ .............................................. C07C 15/16
[52] U.S. Cl. ...................................................... 585/467
[58] Field of Search ........................ 585/467; 568/766

[56] References Cited

U.S. PATENT DOCUMENTS

| | | | |
|---|---|---|---|
| 2,402,092 | 6/1946 | Schmerling et al. | 260/671 |
| 3,941,706 | 3/1976 | Goto et al. | 252/59 |
| 4,251,675 | 2/1981 | Engel | 585/454 |
| 4,339,621 | 7/1982 | Morley | 585/422 |
| 4,439,409 | 3/1984 | Puppe et al. | 423/328 |
| 4,689,436 | 8/1987 | Minokani et al. | 585/422 |
| 4,826,667 | 5/1989 | Zones et al. | 423/277 |
| 4,952,546 | 8/1990 | Knuuttila et al. | 585/467 |
| 4,954,325 | 9/1990 | Rubin et al. | 502/64 |
| 4,962,254 | 10/1990 | Fukao et al. | 585/467 |
| 4,962,256 | 10/1990 | Le et al. | 585/446 |
| 4,982,037 | 1/1991 | Nakamura et al. | 585/446 |
| 5,001,295 | 3/1991 | Angevine et al. | 585/467 |
| 5,003,120 | 3/1991 | Newman et al. | 585/467 |

FOREIGN PATENT DOCUMENTS

| | | |
|---|---|---|
| 202752 | 11/1986 | European Pat. Off. . |
| 231860 | 12/1987 | European Pat. Off. . |
| 293032 | 11/1988 | European Pat. Off. . |

*Primary Examiner*—Anthony McFarlane
*Attorney, Agent, or Firm*—Alexander J. McKillop; Charles J. Speciale; Dennis P. Santini

[57] ABSTRACT

Diarylalkanes are prepared by alkylating an aromatic hydrocarbon with an aromatic alkylation agent in the presence of a synthetic porous crystalline material catalyst composition. The aromatic hydrocarbon can be, for example, benzene, toluene, naphthalene, etc. The aromatic alkylating agent can be an aromatic compound with a hydroxy group, such as phenol, or benzyl alcohol, or an aromatic halide, aldehyde, ether, or an aromatic olefin such as styrene.

22 Claims, No Drawings

METHOD FOR PREPARING DIARYLALKANES

CROSS-REFERENCE TO RELATED APPLICATIONS

This application is a continuation-in-part of U.S. patent application Ser. No. 254,524 filed Oct. 6, 1988, now U.S. Pat. No. 4,954,325 which is a continuation-in-part of U.S. patent application Ser. No. 98,176, filed Sept. 18, 1987, abandoned which is a continuation-in-part of U.S. patent application Ser. No. 890,268 filed July 29, 1986 abandoned. This application is also related by subject matter to U.S. patent application Ser. No. 07/469,999 filed Jan. 25, 1990, and to U.S. patent application Ser. No. 469,998 filed Jan. 25, 1990 now U.S. Pat. No. 4,992,606.

BACKGROUND OF THE INVENTION

This invention relates to an alkylation method for the preparation of diarylalkanes using a synthetic porous crystalline catalyst composition.

Diarylalkanes, such as diphenylmethane, benzyltoluene, and the like, are normally made by the alkylation of aromatic hydrocarbons (e.g., benzene, naphthalene, biphenyls) with aryl halides and alcohols. Diarylalkanes are useful as dielectric impregnants for capacitors, as intermediates in the manufacture of electric insulating, traction and rubber processing oils, as intermediates in the production of pesticides, plasticizers, pharmaceuticals, dyes, and lubricants.

Alkylation reactions are usually carried out at atmospheric pressure with the reactants in the liquid phase, utilizing acid catalysts (e.g. $H_2SO_4$, $BF_3$, $ALCl_3$), metal oxides, or strongly acidic exchange resins. Select aluminosilicates have also been used in the preparation of diarylalkanes.

U.S. Pat. No. 2,402,092 discloses the alkylation of aromatic hydrocarbons with aralkyl halides over silica.

U.S. Pat. No. 3,941,706 describes the preparation of dicyclopentylalkylbenzene functional fluids by treating a lower alkyl substituted benzene such as toluene or ethylbenzene with cyclopentene employing a Friedel-Crafts type catalyst such as aluminum chloride.

U.S. Pat. No. 4,251,675 relates to the preparation of diphenylmethane by reacting benzene and benzyl chloride in the presence of a Friedel-Crafts type catalyst such as ferric chloride.

U.S Pat. No. 4,339,621 discloses the preparation of unsubstituted and alkyl substituted diphenylmethanes by reacting benzene with an alpha-chloromethyl benzene in the presence of sulfuric acid and a cationic surfactant.

U.S. Pat. No. 4,689,436 describes the preparation of alkenyl-aromatic hydrocarbon derivatives by reacting an aromatic hydrocarbon (e.g., benzene, toluene, xylene, tetralin, etc.) with an alkenyl substituted aromatic hydrocarbon (e.g., styrene) in the presence of a heteropolyacid (e.g., phosphotungstic acid, silicomolybodic acid, etc.) and/or a salt thereof.

European Patent Application serial No. 202,752 discloses the preparation of alkylated multi-ring aromatic compounds by reacting the corresponding multi-ring aromatic compound with an alkylating agent, preferably a xylene, in the presence of a zeolite such as ZSM-5, ZSM-11, mordenite, zeolite L and ZSM-4 (zeolite omega).

SUMMARY OF THE INVENTION

A method is provided herein for preparing diarylalkanes from a feedstock containing an aromatic hydrocarbon and an aromatic alkylating agent. This method comprises contacting the aromatic hydrocarbon and the aromatic alkylating agent under alkylation conditions with a catalyst composition which comprises a synthetic porous crystalline material (MCM-22) characterized by an x-ray diffraction pattern including values substantially as set forth in Tables A to D of the specification.

The alkylation conditions include a temperature of from 0° C. to about 550° C., a pressure of from about 0 to 2000 psig, and a space velocity of from about 0.1 to 25 ($hr^{-1}$) WHSV.

Alkylating agents can include aryl olefins, aryl alcohols, aryl halides, aryl hydroxy compounds, aryl aldehydes, and aryl ethers.

DESCRIPTION OF THE PREFERRED EMBODIMENTS

The entire contents of application Ser. Nos. 254,524, 98,176, and 890,268 are incorporated by reference herein.

The term "aromatic" as used herein is to be understood in accordance with its art-recognized scope which includes alky substituted and unsubstituted mono- and polynuclear compounds.

Substituted aromatic compounds which can be alkylated herein must possess at least one hydrogen atom directly bonded to the aromatic nucleus. The aromatic rings can be substituted with one or more alkyl, aryl or alkaryl groups.

Suitable aromatic hydrocarbons include benzene, naphthalene, anthracene, naphthacene, perylene, coronene and phenanthrene.

Generally the alkyl groups which can be present at substituents on the aromatic compound contain from one to about 22 carbon atoms and preferably from about one to eight carbon atoms, and most preferably from about one to four carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene, 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9-10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such product are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate containing substantial qualities of benzene, toluene and/or xylene constitutes a particularly useful feed for the alkylation process of this invention.

Alkylating agents which are useful in the process of this invention generally include aromatic organic compounds having one or more available alkylating groups capable of treating with the alkylatable organic compound. The alkylating agent can be selected from mononuclear compounds, such as benzene derivatives. It can have one or more aliphatic groups attached provided that no group has more than 5 carbon atoms, or it can be without aliphatic constituents. The alkylating group can be an olefinic group, halide, hydroxy, aldehyde, ether, or other known alkylating group. For example, suitable alkylating agents can include benzaldehyde, benzyl chloride, benzyl alcohol, styrene, and related compounds.

Alkylation conditions include a temperature of between 0° C. and 550° C., preferably 50° C. to 500° C., and more preferably 100° C. to 450° C. Pressure can be from 0 to 2000 psig, preferably 25 to 1000 psig, and more preferably 50 to 700 psig. The space velocity can be from 0.1 to 25 ($hr^{-1}$) WHSV, preferably 0.5 to 15 ($hr^{-1}$) WHSV, and more preferably 1 to 10 ($hr^{-1}$) WHSV.

The reaction can be carried out in any of the known reactors usually employed for alkylation. For example, a tubular reactor with a downflow of reactants over a fixed catalyst bed can be employed.

In its calcined form, the synthetic porous crystalline material component employed in the catalyst composition used in the process of this invention is characterized by an X-ray diffraction pattern including the following lines:

TABLE A

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | M-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an x-ray diffraction pattern including the following lines:

TABLE C

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

More specifically, it may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined.

In Tables A-D, the relative intensities are given in terms of the symbols W=weak, M=medium, S=strong, VS=very strong. In terms of intensities, these may be generally designated as follows:

W = 0–20
M = 20–40
S = 40–60
VS = 60–100

It should be understood that these X-ray diffraction patterns are characteristic of all species of the synthetic porous crystalline material. The sodium form as well as other cationic forms reveal substantially the same pattern with some minor shifts in interplanar spacing and variation in relative intensity. Other minor variations can occur depending on the ratio of structural components, e.g., silicon to aluminum mole ratio of the particular sample, as well as its degree of thermal treatment.

Examples of such porous crystalline materials include the PSH-3 compositions of U.S. Pat. No. 4,439,409, incorporated herein by reference, and the crystalline material of U.S. application Ser. No. 254,524, incorporated herein by reference, referred to herein as "MCM-22".

MCM-22 has a composition involving the molar relationship:

$$X_2O_3:(n)YO_2.$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the synthetic porous crystalline material as a result of their presence during crystallization, and are easily removed by post-crystallization methods hereinafter more particularly described.

MCM-22 is thermally stable and exhibits a high surface area greater than about 400m$^2$/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Preferred cations are those which tailor the activity of the catalyst. These include hydrogen, rare earth metals and metals of Groups IIA, IIIA, IVA, IB, IIB, IIIB, IVB and VIII of the Periodic Table of the Elements.

In its calcined form, MCM-22 appears to be made up of a single crystal phase with little or no detectable impurity crystal phases and has an X-ray diffraction pattern including the lines listed in above Tables A-D.

Prior to its use in the catalyst composition herein, the synthetic porous crystalline material should be subjected to thermal treatment to remove part or all of any organic constituent present therein.

The synthetic porous crystalline material present in the catalyst composition herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be associated chemically and/or physically with the MCM-22 and/or matrix with which the MCM-22 may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the synthetic porous crystalline material such as, for example, by, in the case of platinum, treating the synthetic porous crystalline material with a solution containing the platinum metal-containing ion. Thus, suitable platinum compounds for this purpose include chloroplatinic acid, platinous chloride and various compounds containing the platinum amine complex.

The synthetic porous crystalline material, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal temperature can be performed at a temperature of up to about 925° C.

Prior to its use in the catalyst composition and process of this invention, the synthetic porous crystalline material crystals should be at least partially dehydrated. This can be accomplished by heating the crystals to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the crystalline material in a vacuum but a longer time will be required to achieve a suitable degree of dehydration.

MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, or organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |

| -continued | | |
|---|---|---|
| Reactants | Useful | Preferred |
| R/YO$_2$ | 0.05–1.0 | 0.1–0.5 |

In a preferred method of synthesizing MCM-22, the YO$_2$ reactant contains a substantial amount of solid YO$_2$, e.g., at least about 30. wt.% solid YO$_2$. Where YO$_2$ is silica, the use of a silica source containing at least about 30 wt.% solid silica, e.g., Ultrasil (a precipitated, spray dried silica containing about 90 wt.% silica) or HiSil (a precipitated hydrated SiO$_2$ containing about 87 wt.% silica, about 6 wt.% free H$_2$O and about 4.5 wt.% bound H$_2$O of hydration and having a particle size of about 0.02 micron) favors MCM-22 crystal formation from the above mixture and is a distinct difference over the synthesis method disclosed in U.S. Pat. No. 4,439,409. If another source of oxide of silicon, e.g., Q-Brand (a sodium silicate comprised of about 28.8 wt.% of SiO$_2$, 8.9 wt.% Na$_2$O and 62.3 wt.% H$_2$O) is used, crystallization may yield little if any MCM-22 crystalline material and impurity phases of other crystal structures, e.g., ZSM-12, may be produced. Preferably, therefore, the YO$_2$, e.g., silica, source contains at least about 30 wt.% solid YO$_2$, e.g., silica, and more preferably at least about 40 wt.% solid YO$_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 material will vary with the nature of the reaction mixture employed and the crystallization conditions. In all cases, synthesis of the MCM-22 crystals is facilitated by the presence of at least about 0.01 percent, preferably about 0.10 percent and still more preferably about 1 percent, seed crystals based on the total weight of the crystalline product formed.

The synthetic porous crystalline material crystals can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desirable to incorporate the synthetic porous crystalline material with another material, i.e., a binder, which is resistant to the temperatures and other conditions employed in the process of this invention. Suitable binder materials include active and inactive materials and synthetic or naturally occurring zeolite as well as inorganic materials such as clays, silica and/or metal oxides such as alumina. The latter can be either naturally occurring or provided in the form of gelatinous precipitates or gels including mixtures of silica and metal oxides. Use of a binder material in conjunction with the synthetic porous crystalline material, i.e., combined therewith or present during its synthesis, which itself is catalytically active may change the conversion and/or selectivity of the catalyst. Inactive materials suitable serve as diluents to control the amount of conversion so that products can be obtained economically and in a controlled fashion without having to employ other means for controlling the rate of reaction.

These materials can be incorporated into naturally occurring clays, e.g., bentonite and kaolin, to improve the crush strength of the synthetic porous crystalline material under commercial operating conditions. Good crush strength is an advantageous attribute for commercial use since it prevents or delays breaking down of the catalyst into powder-like materials.

Naturally occurring clays which can be composited with the synthetic porous crystalline material include the montmorillonite and kaolin family, which families include the subbentonites, and the kaolines commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the synthetic porous crystalline material also include inorganic oxides, notably alumina.

Apart from or in addition to the foregoing binder materials, the synthetic porous crystalline material can be composited with an inorganic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may also be advantageous to provide at least a part of the foregoing matrix materials in colloidal form so as to facilitate extrusion of the bound catalyst component(s).

The relative proportions of finely divided crystalline material and inorganic oxide matrix can vary widely with the MCM-22 content ranging from about 1 to about 95 percent by weight and more usually, particularly when the composite is prepared in the form of beads, in the range of about 2 to about 80 weight percent of the composite.

The utility of MCM-22 may be increased by combining the as-synthesized MCM-22 with binder, converting the bound MCM-22 to the hydrogen form (i.e., HMCM-22) and steaming the bound HMCM-22 composition under conditions sufficient to increase the stability of the catalyst. U.S. Pat. Nos. 4,663,492; 4,594,146; 4,522,929; and, 4,429,176, the entire disclosures of which are incorporated herein by reference, describe conditions for the steam modification of zeolite catalysts which can be utilized to steam-modify bound MCM-22. The steaming conditions include contacting the bound MCM-22 with steam (e.g., 5–100%) at a temperature of at least about 300° C. for at least one hour at a pressure of 101–2,500 kPa. In a more particular embodiment, the catalyst can be made by steaming with 75–100% steam at 315°–500° C. and atmospheric pressure for 2–25 hours. In accordance with the steam stabilization treatment described in the above-mentioned patents, the steaming of the catalyst can take place under conditions sufficient to initially increase the Alpha Value of the catalyst, the significance of which is discussed infra, and produce a steamed catalyst having a peak Alpha Value. If desired, steaming can be continued to subsequently reduce the Alpha Value from the peak Alpha Value to an Alpha Value which is substantially the same as the Alpha Value of the unsteamed catalyst.

In order to more fully illustrate the process of this invention and the manner of practicing same, the following examples are presented. Whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample g/100 g of calcined adsorbant. MCM-22 always exhibits Equilibrium Adsorption values of greater than about 10 wt.% for water vapor, greater than about 4.5 wt.% (and usually greater than about 7 wt.%) for cyclohexane vapor and greater than about 10 wt.% for n-hexane vapor. These vapor sorption capacities are a notable distinguishing feature of MCM-22 and are prepared for the component of catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant $=0.016$ sec$^{-1}$). The Alpha Test is described in U.S. Pat. No. 3,354,078; in the *Journal of Catalysis*, vol. 4, p. 527 (1965); vol. 6, p. 278 (1966): and vol. 61, p. 395 (1980), each inoorporated herein by reference as to that description. The experimental conditions of the test used herein include a constant temperature of 538° C. and a variable flow rate as described in detail in the *Journal of Catalysis*, vol. 61, p. 395.

EXAMPLE 1

One part sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (90% $SiO_2$).

The reaction mixture had the following composition, in mole ratios:

$SiO_2/Al_2O_3 = 30.0$
$OH/SiO_2 = 0.18$
$H_2O/SiO_2 = 44.9$
$Na/SiO_2 = 0.18$
$R/SiO_2 = 0.35$
where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

| | |
|---|---|
| $H_2O$ | 15.2 wt. % |
| Cyclohexane | 14.6 wt. % |
| n-Hexane | 16.7 wt. % |

The surface area of the synthetic porous crystalline material was measured to be 494 $m^2/g$.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio | 21.10 |

TABLE E

| Degrees 2-Theta | Interplanar d-Spacing (A) | $I/I_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surface area measurements were of the calcined product.

TABLE F

| Example | 3 | 4 | 5 |
| --- | --- | --- | --- |
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2O/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and respectively.

EXAMPLE 7

To demonstrate a larger preparation of the required synthetic porous crystalline material 4.5 parts of hexamethyleneimine was added to a solution containing 1.0 parts of sodium aluminate, 1.0 part of 50% NaOH solution and 44.2 parts of $H_2O$. To the combined solution was added 8.5 parts of precipitated silica (Ultrasil VN3). The mixture was crystallized with agitation at 145° C. in a reactor and the product was water washed and dried at 120° C.

The X-ray diffraction pattern of the dried product crystals demonstrates the product to be the crystalline material of this invention. Product chemical composition (uncalcined) surface area and adsorption analyses results were as set forth in Table G:

TABLE G

| Product Composition | |
| --- | --- |
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3g samples of the calcined material ion-exchanged 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions Ionic Composition, wt. % | TEA | TPA | La |
| --- | --- | --- | --- |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the synthetic porous crystalline material had very good stability under severe hydrothermal treatment.

EXAMPLE 11

This example illustrates the preparation of the present synthetic porous crystalline material where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

$SiO_2/B_2O_3 = 6.1$
$OH/SiO_2 = 0.06$
$H_2O/SiO_2 = 19.0$
$K/SiO_2 = 0.06$
$R/SiO_2 = 0.30$ where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 240° C. and found to have the following sorption capacities:

| $H_2O$ | 11.7 wt. % |
| --- | --- |
| Cyclohexane | 7.5 wt. % |
| n-Hexane | 11.4 wt. % |

The surface area of the calcined crystalline material was measured (BET) to be 405 $m^2/g$.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio | 1406 |
| $SiO_2/(Al + B)_2O_3$, molar ratio | 25.8 |

EXAMPLE 12

A portion of the calcined crystalline product of Example 11 was treated with $NH_4Cl$ and again calcined. The final crystalline product was tested in the Alpha test and found to have an Alpha Value of 1.

EXAMPLE 13

This examples illustrates another preparation of the synthetic porous crystalline material in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

$SiO_s/B_2O_3 = 12.3$
$OH/SiO_2 = 0.056$
$H_2O/SiO_2 18.6$
$K/SiO_2 = 0.056$
$R/SiO_2 = 0.30$ where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ | 14.4 wt. % |
| Cyclohexane | 4.6 wt. % |
| n-Hexane | 14.0 wt. % |

The surface area of the calcined crystalline material was measured to be 438m²/g.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | 249 |
| $SiO_2/(Al + B)_2O_3$, molar ratio | 28.2 |

EXAMPLE 14

A portion of the calcined crystalline product of Example 13 was tested in the Alpha Test and found to have an Alpha Value of 5.

EXAMPLE 15

A 65% MCM-22/35% $Al_2O_3$ extrudate with an alpha value of about 250 was crushed, sized to 24/40 mesh and charged to a reactor. The MCM-22 was prepared in accordance with the method of Example 7, above. The reactor was pre-heated to 300° F. in flowing nitrogen. A mixture of benzene and benzyl alcohol in a 11.4:1 molar ratio was charged to the reactor. Process conditions were: WHSV (benzene + benzyl alcohol) = 10 hr$^{-1}$, $N_2$:benzene (molar)=4.7, 300° F. and 0 psig. After 30 minutes the liquid reaction products were collected and analyzed. Table H below summarizes the results of the product analysis.

A 65% ZSM-5/35% $Al_2O_3$ extrudate with an alpha value of about 250 was crushed, sized to 24/40 mesh and charged to a reactor. The reactor was pre-heated to 300° F. in flowing nitrogen. A mixture of benzene and benzyl alcohol in a 11.4:1 molar ratio was charge to the reactor. Process conditions were WHSV (benzene + benzyl alcohol) = 10 hr$^{-1}$, $N_2$:benzene (molar)=4.7, 300° F. and 0 psig. After 30 minutes the liquid reaction products were collected and analyzed. Table H below summarizes the results of the product analysis. At comparable activity levels the ZSM-5 catalyst is less selective for the formation of diphenylmethane than the MCM-22 catalyst.

TABLE H

Synthesis of diphenylmethane over MCM-22 and ZSM-5

| Zeolite | Benzyl Alcohol Conversion | Diphenylmethane Selectivity* |
|---|---|---|
| MCM-22 | 97 | 45 |
| ZSM-5 | 98 | 31 |

*Molar Selectivity Based on Benzyl Alcohol Conversion

The Benzyl Alcohol Conversion and the Diphenylmethane Selectivity were calculated in accordance with the following formulae:

Benzyl Alcohol Conversion =

$$\frac{(\text{wt \% benzyl alcohol in feed}) - (\text{wt \% benzyl alcohol in product})}{(\text{wt \% benzyl alcohol in feed})} \times 100$$

Diphenylmethane Selectivity =

$$\frac{\text{moles of diphenylmethane produced}}{\text{moles of benzyl alcohol converted}} \times 100$$

What is claimed is:

1. A process for producing a diarylalkane from a feedstock containing at least one alkylatable aromatic hydrocarbon compound and an aromatic alkylating agent having at least one alkylating group, said process comprising contacting said feedstock with a catalyst composition under alkylation reaction conditions to produce an alkylate product containing at least one diarylalkane compound, and said catalyst composition comprising a synthetic porous crystalline material characterized by an X-ray diffraction pattern including values substantially as follows:

| Interplanar d-Spacing (A) | Relative Intensity, I/I° × 100 |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | M-M |
| 4.06 ± 0.07 | W-S |
| 3.91 ± 0.07 | M-VS |

| Interplanar d-Spacing (A) | Relative Intensity, I/I° × 100 |
|---|---|
| 3.42 ± 0.06 | VS |

2. The process of claim 1 wherein said synthetic porous crystalline material is characterized by an X-ray diffraction pattern including values substantially as follows:

| Interplanar d-Spacing (A) | Relative Intensity, I/I° × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

3. The process of claim 1 wherein the synthetic porous crystalline material is characterized by an X-ray diffraction pattern including values substantially as follows:

| Interplanar d-Spacing (A) | Relative Intensity, I/I° × 100 |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

4. The process of claim 1 wherein the synthetic porous crystalline material is characterized by an X-ray diffraction pattern including values substantially as follows:

| Interplanar d-Spacing (A) | Relative Intensity, I/I° × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

5. The process of claim 1 wherein the synthetic porous crystalline material has a composition comprising the molar relationship:

$$X_2O_3:(n)YO_2$$

wherein X is a trivalent element selected from the group consisting of aluminum, boron, iron and gallium, Y is a tetravalent element selected from the group consisting of silicon and germanium, and n is at least about 10.

6. The process of claim 2 wherein the synthetic porous crystalline material has a composition comprising the molar relationship:

$$X_2O_3:(n)YO_2$$

wherein X is a trivalent element selected from the group consisting of aluminum, boron, iron and gallium, Y is a tetravalent element selected the group consisting of silicon and germanium, and n is at least about 10.

7. The process of claim 3 wherein the synthetic porous crystalline material has a composition comprising the molar relationship:

$$X_2O_3:(n)YO_2$$

wherein X is a trivalent element selected from the group consisting of aluminum, boron, iron and gallium, Y is a tetravalent element selected from the group consisting of silicon and germanium, and n is at least about 10.

8. The process of claim 4 wherein the synthetic porous crystalline material has a composition comprising the molar relationship:

$$X_2O_3:(n)YO_2$$

wherein X is a trivalent element selected from the group consisting of aluminum, boron, iron and gallium, Y is a tetravalent element selected from the group consisting of silicon and germanium, and n is at least about 10.

9. The process of claim 1, wherein the synthetic porous crystalline material possesses equilibrium absorption capacities greater than about 4.5 weight percent for cyclohexane vapor and greater than about 10 weight percent for n-hexane vapor.

10. The process of claim 1 wherein said synthetic porous crystalline material has been treated to replace original cations, at least in part, with a cation or mixture of cations selected from the group consisting of hydrogen, rare earth metals, and metals of Groups IIA, IIIA, IVA, IB, IIB, IIIB, IVB and VIII of the Periodic Table.

11. The process of claim 10 wherein said synthetic porous crystalline material has been thermally treated in the presence or absence of steam at a temperature of up to about 925° C.

12. The process of claim 1 wherein said synthetic porous crystalline material has been thermally treated in the presence or absence of steam at a temperature of up to about 925° C.

13. The process of claim 1 wherein said alkylatable aromatic compound is selected from the group consisting of benzene, naphthalene, anthracene, naphthacene, perylene, coronene and phenanthrene.

14. The process of claim 1 wherein the alkylatable aromatic compound is selected from the group consisting of toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene, 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9-10-dimethylphenanthrene; and 3-methyl-phenanthrene.

15. The process of claim 1 wherein the alkylating agent is an olefin.

16. The process of claim 1 wherein the alkylating agent is an alcohol.

17. The process of claim 1 wherein the alkylating agent is an alkyl halide.

18. The process of claim 1 wherein said alkylating conditions include a temperature of between about 0° C. and 550° C., a pressure of between about 0 and 2000 psig, and a space velocity of between about 0.1 and 25 $hr^{-1}$ WHSV.

19. The process of claim 1 wherein said alkylation conditions include a temperature of between about 50° C. and 500° C., a pressure of between about 25 and 1000 psiq, and a space velocity of between about 0.5 and 15 $hr^{-1}$ WHSV.

20. The process of claim 1 wherein said alkylation conditions include a temperature of between about 100° C. and 450° C., a pressure of between about 50 and 700 psig, and a space velocity of between about 1 and 10 $hr^{-1}$ WHSV.

21. The process of claim 1 wherein said catalyst composition includes a matrix material.

22. The process of claim 21 wherein said matrix material is selected from the group consisting of silica, alumina, zirconia, titania, magnesia, beryllia, thoria, and combinations thereof.

* * * * *